United States Patent [19]

Kobzina

[11] Patent Number: 4,465,502

[45] Date of Patent: * Aug. 14, 1984

[54] HERBICIDAL N-HALOACETYL-2-SUBSTITUTED-6-ACYLANILINES

[75] Inventor: John W. Kobzina, Walnut Creek, Calif.

[73] Assignee: Chevron Research Company, San Francisco, Calif.

[*] Notice: The portion of the term of this patent subsequent to Jan. 13, 1998 has been disclaimed.

[21] Appl. No.: 414,763

[22] Filed: Sep. 7, 1982

Related U.S. Application Data

[60] Continuation-in-part of Ser. No. 211,618, Dec. 1, 1980, abandoned, which is a continuation-in-part of Ser. No. 172,788, Jul. 28, 1980, Pat. No. 4,348,222, which is a division of Ser. No. 53,877, Jul. 2, 1979, Pat. No. 4,244,730.

[51] Int. Cl.$^3$ ............................................. A01N 43/28
[52] U.S. Cl. ............................................. 71/76; 71/88; 549/373; 549/452
[58] Field of Search ............... 71/88, 76; 549/373, 549/452

[56] References Cited

U.S. PATENT DOCUMENTS

| 3,294,818 | 12/1966 | Bobowski et al. | 260/340.9 |
| 3,792,062 | 2/1974 | Teach | 549/452 |
| 4,116,670 | 9/1978 | Stach et al. | 71/88 |
| 4,244,730 | 1/1981 | Kobzina | 71/88 |
| 4,261,733 | 4/1981 | Chupp | 549/373 |

Primary Examiner—Paul M. Coughlan, Jr.
Attorney, Agent, or Firm—S. R. LaPaglia; T. G. DeJonghe; L. S. Squires

[57] ABSTRACT

Compounds of the formula:

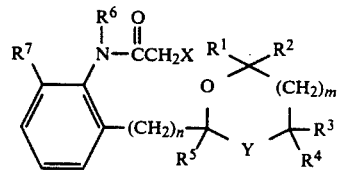

wherein

X is halo; m and n are 0 or 1; $R^1$ and $R^3$ are hydrogen, alkyl or are joined to form a carbocyclic ring; $R^2$ and $R^4$ are hydrogen or alkyl; $R^5$ and $R^6$ are hydrogen, alkyl or alkoxyalkyl; $R^7$ is hydrogen, halo, nitro, alkoxy or alkyl; and Y is oxygen or $NR^8$ wherein $R^8$ is hydrogen or alkyl, have herbicidal and growth-regulating activity, particularly against grassy weeds.

14 Claims, No Drawings

HERBICIDAL N-HALOACETYL-2-SUBSTITUTED-6-ACYLANILINES

CROSS-REFERENCE TO RELATED APPLICATION

This application is a continuation-in-part of Ser. No. 211,618, filed Dec. 1, 1980, now abandoned, which is a continuation-in-part of Ser. No. 172,788, filed July 28, 1980, now U.S. Pat. No. 4,348,222, which in turn is a division of Ser. No. 53,877, filed July 2, 1979, now U.S. Pat. No. 4,244,730, the disclosures of all which are hereby incorporated by reference in their entirety.

BACKGROUND OF THE INVENTION

U.S. Pat. No. 4,141,989 discloses 3-(N-chloro-acetyl)-N-(2,6-dialkylphenylamino)-gamma-butyrolactones as fungicides.

U.S. Pat. No. 4,055,410 discloses substituted bromo and chloroacetamides as herbicides.

In *Chem. Abstr.*, 92:58400W (1980), there are disclosed herbicidal 3-[3'-alkyl-2'-(N-haloacetylalkoxymethylamino)phenyl]-propionaldehyde O,O-dialkyl acetals.

SUMMARY OF THE INVENTION

This invention relates to novel N-haloacetyl-2-substituted-6-acylaniline compounds and methods of their use as herbicides and plant-growth regulators. It has now been found that the placement of certain acyl, ketal, oxime, hydroxyalkyl and alkoxyalkyl substituents on the 6-position of N-haloacetyl-2-substituted anilines results in compounds having herbicidal and plant-growth regulating activity. The compounds of the invention are particularly effective for pre-emergent treatment of grassy weeds.

DESCRIPTION OF THE INVENTION

The compounds of the invention are represented by the formula:

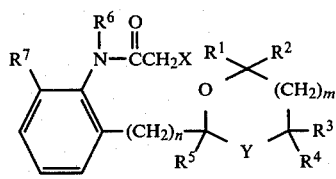

(I)

wherein

X is halo; n and m are individually 0 or 1;

$R^1$ and $R^3$ are individually hydrogen or alkyl of 1 to 4 carbon atoms or $R^1$ and $R^3$ joined to form a carbocyclic ring containing 5 to 10 carbon atoms; $R^2$ and $R^4$ are individually hydrogen, alkyl of 1 to 4 carbon atoms, phenyl or phenyl substituted with 1 to 4 halo, alkyl of 1 to 4 carbon atoms, alkoxy of 1 to 4 carbon atoms or nitro groups;

$R^5$ and $R^6$ are individually hydrogen, alkyl of 1 to 4 carbon atoms or alkoxyalkyl of 2 to 6 carbon atoms; $R^7$ is hydrogen, halo, nitro, alkylthio of 1 to 4 carbon atoms, alkoxy of 1 to 4 carbon atoms or alkyl of 1 to 4 carbon atoms; and Y is oxygen or $NR^8$, wherein $R^8$ is hydrogen or alkyl of 1 to 4 carbon atoms.

Representative $R^1$, $R^2$, $R^3$, $R^4$, $R^5$, $R^6$, and $R^8$ alkyl groups are methyl, ethyl, 1-propyl, n-propyl, n-butyl, sec-butyl, i-butyl. Representative $R^1$-$R^3$ carbocyclic linkages are $-CH_2CH_2-$, $-(CH_2)_3-$, $-(CH_2)_4-$, $-(CH_2)_6-$, and $-(CH_2)_8-$. Representative $R^2$ and $R^4$ phenyl groups are phenyl, p-chlorophenyl, 3,5-dichlorophenyl, 4-methylphenyl, 4-methoxyphenyl. Preferably, $R^1$ is alkyl of 1 to 4 carbon atoms and $R^2$, $R^3$ and $R^4$ are hydrogen or alkyl of 1 to 4 carbon atoms.

Representative $R^5$ and $R^6$ alkoxyalkyl groups are methoxymethyl, methoxyethyl, ethoxymethyl, ethoxyethyl, methoxypropyl, ethoxybutyl, methoxypentyl.

Preferably, $R^5$ is alkyl of 1 to 4 carbon atoms, and most preferably, $R^5$ is methyl.

Preferably, $R^6$ is hydrogen.

Other representative $R^7$ groups are chloro, bromo, fluoro, nitro, methoxy methylthio, ethoxy, propoxy, propylthio, butoxy. Preferably, $R^7$ is alkyl of 1 to 4 carbon atoms.

Representative X groups are chloro, bromo, fluoro, iodo. Preferably, X is chloro.

Preferably, Y is oxygen and n and m are both zero.

The compound Formula I, wherein one of $R^1$, $R^2$ $R^3$ or $R^4$ is methyl and the rest are hydrogen, $R^5$ is methyl, $R^6$ is methyl, $R^7$ is methyl, m is 0, n is 0, X is chloro and Y is oxa, exhibits especially excellent pre-emergent herbicidal activity against grasses.

The compounds of the invention may be made according to the following scheme:

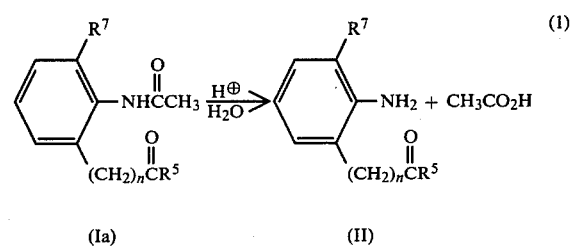

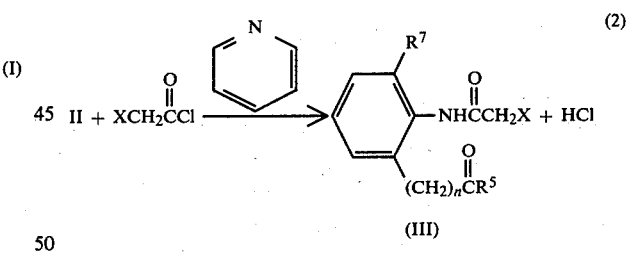

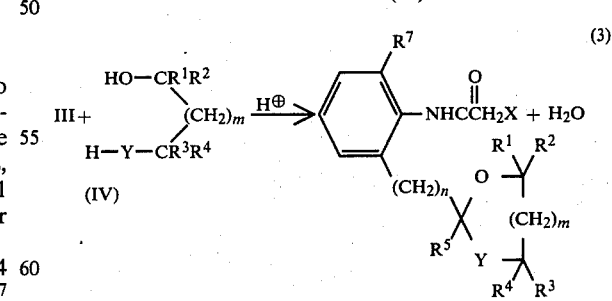

wherein $R^1$, $R^2$, $R^3$, $R^4$, $R^5$, $R^6$, $R^7$, Y, X, m and n are as defined hereinabove and Z is bromo or chloro.

The above reactions are conventional deacetylation (1), acetylation (2), ketalization (3) and alkylation (4) reactions and may be performed by known procedures. As well as using alkyl halide, the alkylation reaction can also be effected via conventional procedures using the appropriate dialkyl sulfate and n-butyl lithium.

In the case wherein $R^5$ is hydrogen, my preferred method is as follows:

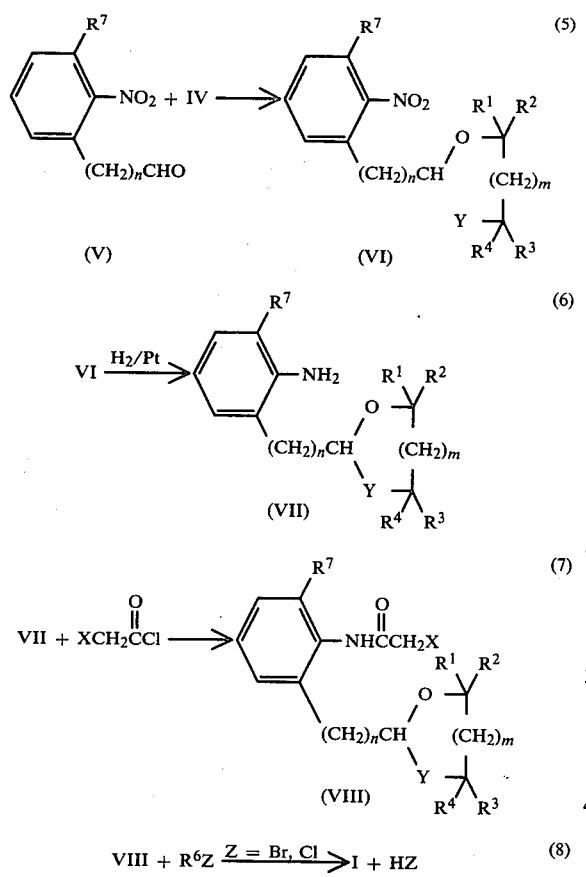

wherein $R^1$, $R^2$, $R^3$, $R^4$, $R^5$, $R^6$, $R^7$, X, Y, m and n are as defined hereinabove and Z is bromo or chloro.

Reaction conditions for reactions (5), (7) and (8) are similar to those of reactions (3), (2) and (4), respectively. Also, if desired, the alkylation step can be effected prior to arylation using compound VII as the starting material. Reaction (6) may be performed under conventional hydrogenation conditions with platinum catalyst.

The compounds of the present invention are, in general, herbicidal and plant-growth regulating in both pre- and post-emergent applications, but are particularly effective in pre-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broad-leaved weeds. Some may be selective with respect to the type of application and/or type of weed. The compounds of the invention are particularly effective as pre-emergent herbicides against weed grasses.

The compounds, when applied to growing plants above the ground in such an amount that the compounds will not kill beneficial plants, also show efficient plant growth regulating or retarding effects and may be advantageously employed, for example, to prevent or retard the growth of turf grass.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbicidal compositions can be used. The active ingredient usually makes up from 0.5 to 90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

The amount of compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent herbicidal control, the compounds of the invention are applied at rates of 0.2 to 60 kg/ha, and the preferred rate is in the range of 0.5 to 40 kg/ha. For plant growth regulating or retarding activity, it is essential to apply the oxime compounds at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Herbicidal tests on representative compounds of the invention were made using the following methods.

PRE-EMERGENT HERBICIDAL TEST

An acetone solution of the test compound was prepared by mixing 375 mg of the compound, 118 mg of a nonionic surfactant and 18 ml of acetone. Ten ml of this solution was added to 40 ml of water to give the test solution.

Seeds of the test vegetation were planted in a pot of soil and the test solution was sprayed uniformly onto the soil surface at a dose of 27.5 micrograms/cm². The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table I. The compounds were also tested at lower dosages on weeds and crops. The results of these tests appear in Table II.

POST-EMERGENT HERBICIDAL TEST

The test compound was formulated in the same manner as described above for the pre-emergent test. This formulation was uniformly sprayed on 2 similar pots of 24-day-old plants (approximately 15 to 25 plants per pot) at a dose of 27.5 micrograms/cm². After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table I.

PLANT-GROWTH REGULATION TEST

Four turf grass species shown in Table III were grown in rows in 6.5×9.5" pots to a height of 4 to 6", then were trimmed to a height of one inch. Each test compound was uniformly sprayed on the turf grass species at the test concentrations. After 20 days in the greenhouse under normal watering and fertilization, each species was cut one inch above soil level and weighed. Weights are expressed as % growth inhibition compared to untreated check species. Four replicates were used per treatment.

EXAMPLE 1

Preparation of
N-Chloroacetyl-2-methyl-6-acetylaniline

A. N-acetyl-2-methyl-6-acetylaniline (76.1 g) in water (300 ml), ethanol (300 ml), concentrated hydrochloric acid (300 ml) and concentrated sulfuric acid (15 ml) were refluxed for 24 hours. The solution was cooled and concentrated ammonium hydroxide was added to pH 10. The solution was extracted with dichloromethane. The extracts were dried (MgSO₄) and stripped. 2-Methyl-6-acetylaniline (49.3 g) was obtained as a tan solid.

B. 2-Methyl-6-acetylaniline (25 g) and pyridine (26.5 g) in 1 liter methylene chloride were cooled in an ice-acetone bath. A solution of chloroacetyl chloride (37.9 g) in 100 ml methylene chloride was dripped in slowly. The solution was stirred at room temperature for 2 hours, washed with 10% HCl, 10% NaOH, dried (MgSO₄) and stripped. Yield: The title product as a white solid, MP 88°–89° C.

EXAMPLE 2

Preparation of
2,4-Dimethyl-2-(3-methyl-2-chloroacetamidophenyl) dioxolane

N-chloroacetyl-2-methyl-6-acetylaniline (from Example 1), 4.51 g, 1,2-propanediol, 3.7 ml, and a dash of toluene sulfonic acid were combined in 50 ml toluene and refluxed. The distilled water by-product was collected in a Dean-Stark trap. After water ceased to distil, methylene chloride was added and the mixture was extracted successively with bicarbonate solution and water, then dried (MgSO₄) and evaporated to yield 3.3 g brown oil. The oil was purified on a silica gel column (Hexane:ethyl acetate eluant) to yield the title product (Compound No. 2 in Table A).

EXAMPLE 3

Preparation of
2,4,4,5-Tetramethyl-2-(3-methyl-2-chloroacetamidophenyl) dioxolane The procedure of Example 2 was used employing 2-methyl-butane-2,3-diol instead of 1,2-propanediol.

The product was purified on a silica gel column to yield the title product (Compound No. 3 in Table A).

EXAMPLE 4

Preparation of
2-Methyl-4-ethyl-2-(3'-methyl-2'-chloroacetamido-phenyl) dioxolane The procedure of Example 2 was used employing 1,2-butanediol instead of 1,2-propanediol.

The product was purified on a silica gel column to yield the title product (Compound No. 1 in Table A).

EXAMPLE 5

Preparation of
2,4-Dimethyl-2-[3-methyl-2-(N-methyl-chloroacetamido)phenyl]dioxolane 15.0 g (0.053 mol) of 2,4-dimethyl-2-(3-methyl-2-chloroacetamido)phenyl-dioxolane was dissolved in 200 ml of tetrahydrofuran at room temperature and then cooled to −70° C. 37.5 ml of an n-butyl lithium mixture containing 0.060 mole of n-butyl lithium was then added dropwise at −70°-60° C. The resulting mixture was stirred for 15 minutes at −75° C. and 6 ml (0.060 mole) of dimethyl sulfate was added dropwise. The mixture was allowed to slowly warm to room temperature and then mixed with ethyl ether and 200 ml of water resulting in phase separation. The water layer was separated from the ethyl ether layer and washed with ethyl ether. The washings were combined with the ethyl ether layer and then washed three times with water dried over sodium sulfate and magnesium sulfate and evaporated to a dark oil. NMR examination showed the presence of the dioxolane starting material. Accordingly, the oil was dissolved in tetrahydrofuran cooled to −70° C. and 15 ml of n-butyl lithium in hexane mixture containing 0.024 mole of n-butyl lithium was added. After a few minutes 5 ml (0.050 mole) of dimethyl sulfate was added and the mixture then allowed to warm to room temperature and left overnight (about 15 hours). The mixture was exhibited, washed, dried and evaporated as before. Thin layer chromatographic examination of a sample of the residue showed no traces of the dioxolane starting material. The residue was then chromatographed over silica eluting with hexane, ethyl acetate mixtures. The product fractions were evaporated under vacuum affording an oil which was then distilled under vacuum affording 10.6 g of the title compound as an oil.

The temperature of the mixture was allowed to raise to 25° C., then refluxed for 3 hours and then stirred overnight (about 15 hours) at room temperature. The mixture was then mixed with about 500 ml of water and extracted with ethyl ether. The ethyl ether extracts were combined, dried over magnesium sulfate and evaporated to dryness affording the title compound as an oil.

EXAMPLE 7

By following the appropriate procedures set forth in Examples 1–6 but using the appropriate starting materials, the compounds listed in Table A hereinbelow were prepared.

TABLE A

Compounds of the Formula:

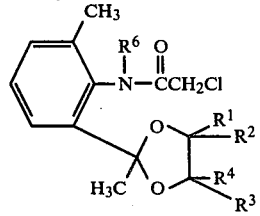

| No. | $R^1$ | $R^2$ | $R^3$ | $R^4$ | $R^6$ | m.p. °C. | C Cal. | C Fd. | H Cal. | H Fd. | N Cal. | N Fd. |
|---|---|---|---|---|---|---|---|---|---|---|---|---|
| 1 | $C_2H_5$ | H | H | H | H | Oil | 60.5 | 61.4 | 6.8 | 7.5 | 4.7 | 4.5 |
| 2 | $CH_3$ | H | H | H | H | Oil | 59.26 | 57.93 | 6.39 | 6.58 | 4.94 | 5.16 |
| 3 | $CH_3$ | $CH_3$ | $CH_3$ | H | H | Oil | 61.6 | 60.1 | 7.1 | 7.2 | 4.5 | 4.5 |
| 4 | $C_2H_5$ | H | H | $C_2H_5$ | H | Oil | 62.7 | 67.3 | 7.4 | 8.0 | 4.3 | 4.4 |
| 5 | $CH_3$ | H | $CH_3$ | H | H | 55–57 | 60.50 | 58.94 | 6.77 | 6.63 | 4.7 | 4.58 |
| 6 | H | H | H | H | H | Oil | — | — | — | — | 13.1* | 11.7* |
| 7 | H | H | H | $CH_3$ | $CH_3$ | Oil | 60.5 | 60.7 | 6.8 | 7.0 | 4.7 | 4.5 |
| 8 | H | $CH_3$ | H | $CH_3$ | $CH_3$ | Oil | 61.6 | 61.7 | 7.1 | 7.7 | 4.5 | 4.2 |

*Chlorine

EXAMPLE 6

Preparation of 2,4-Dimethyl-2-(2-methyl-N-methylanilino)dioxolane (a) 2,4-Dimethyl-2-(2-methylanilino)dioxolane was prepared by following the procedure of Example 2 but using 2-methyl-6-actylaniline in place of N-chloroacetyl-2-methyl-6-acetylaniline.

(b) 10.0 g (0.048 mole) of 2,4-dimethyl-2-(2-methylanilino)dioxolane was dissolved in about 150 ml of tetrahydrofuran and then cooled to −60° C. 30.15 ml of 1.6 molar n-butyl lithium in hexane (0.048 mole of n-butyl lithium) was added and the temperature of the mixture allowed to raise to 0° C. 4.6 ml (0.048 mole) of dimethyl sulfate was added dropwise at about 0°–10° C.

TABLE I

HERBICIDAL ACTIVITY @ 27.5 GAMMA/CM²
Pre/Post % Control

| No. | L | M | P | C | W | O |
|---|---|---|---|---|---|---|
| 1 | 60/0 | 70/0 | 55/0 | —/10 | 100/65 | 75/0 |
| 2 | 100/0 | 75/0 | 75/0 | 100/20 | 100/35 | 100/10 |
| 3 | 85/0 | 95/0 | 85/0 | 100/0 | 100/0 | 90/0 |
| 7 | 100/40 | 97/70 | 100/40 | 100/58 | 100/75 | 100/55 |
| 8 | 93/20 | 68/50 | 68/50 | 100/65 | 100/65 | 98/48 |

L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochola crusgalli*)
O = Wild Oats (*Avenua fatua*)

TABLE II

PRE-EMERGENT HERBICIDAL ACTIVITY
% PHYTOTOXICITY

| No. | gamma cm² | SOYBEANS | RICE | L | M | P | C | W | O |
|---|---|---|---|---|---|---|---|---|---|
| 1 | 4.4 | 0 | 62 | 20 | 53 | 0 | 100 | 98 | 68 |
|   | 1.8 | 0 | 7 | 0 | 0 | 0 | 88 | 95 | 7 |
|   | 0.7 | 0 | 0 | 0 | 0 | 0 | 37 | 70 | 0 |
| 2 | 4.4 | 25 | 90 | 47 | 73 | 25 | 100 | 100 | 83 |
|   | 1.8 | 10 | 38 | 0 | 53 | 0 | 100 | 95 | 60 |
|   | 0.7 | 0 | 2 | 0 | 0 | 0 | 70 | 92 | 0 |
| 3 | 4.4 | 5 | 63 | 85 | 85 | 0 | 100 | 100 | 77 |
|   | 1.8 | 0 | 3 | 53 | 10 | 0 | 94 | 90 | 0 |
|   | 0.7 | 0 | 0 | 0 | 0 | 0 | 33 | 60 | 0 |
| 7 | 4.4 | 25 | 92 | 100 | 90 | 100 | 100 | 100 | 100 |
|   | 1.8 | 7 | 50 | 100 | 99 | 100 | 100 | 100 | 87 |
|   | 0.7 | 2 | 7 | 52 | 10 | 98 | 77 | 95 | 33 |

TABLE II-continued

PRE-EMERGENT HERBICIDAL ACTIVITY
% PHYTOTOXICITY

| No. | gamma cm² | SOYBEANS | RICE | L | M | P | C | W | O |
|---|---|---|---|---|---|---|---|---|---|
|  | 0.28 | 0 | 3 | 0 | 0 | 20 | 42 | 75 | 7 |
| 8 | 4.4 | 0 | 73 | 52 | — | 100 | 100 | 100 | 98 |
|  | 1.8 | 0 | 53 | 13 | — | 100 | 93 | 100 | 68 |
|  | 0.7 | 0 | 30 | 0 | — | 98 | 80 | 93 | 13 |
|  | 0.28 | 0 | 0 | 0 | — | 75 | 28 | 82 | 0 |
| A* | 4.4 | 0 | 100 | 100 | 47 | 100 | 100 | 100 | 93 |
|  | 1.8 | 0 | 97 | 35 | 0 | 96 | 95 | 100 | 72 |
|  | 0.7 | 0 | 23 | 0 | 0 | 52 | 78 | 99 | 42 |
|  | 0.28 | 0 | 0 | 0 | 0 | 0 | 58 | 62 | 0 |

*Alachlor ® - 2-chloro-2',6'-diethyl-N—(methoxymethyl)acetanilide.

TABLE III

Pre-Emergence Herbicidal Activity
Expanded Weed Species Tests
% Phytotoxicity

| Compound No. | Dosage gamma cm² | Broad Leaf | | | | | Grasses | | | | | |
|---|---|---|---|---|---|---|---|---|---|---|---|---|
|  |  | F.B.* | Jw.* | P.S.* | Sp.* | Sw.* | Cheat Grass | Johnson Grass | Rye Grass | Switch Grass | Yellow Foxtail | Yellow Nutsedge |
| 7 | 4.4 | 7 | 65 | 88 | 53 | 100 | 100 | 98 | 100 | 100 | 100 | 100 |
|  | 1.8 | 0 | 7 | 60 | 7 | 97 | 100 | 95 | 100 | 100 | 100 | 100 |
|  | 0.7 | 0 | 0 | 10 | 0 | 58 | 77 | 57 | 90 | 100 | 100 | 83 |
|  | 0.28 | 0 | 0 | 0 | 0 | 20 | 0 | 33 | 35 | 93 | 87 | 50 |
| 8 | 4.4 | 0 | 48 | 65 | 20 | 100 | 100 | 100 | 100 | 100 | 100 | 100*¹ |
|  | 1.8 | 0 | 0 | 53 | 0 | 93 | 93 | 95 | 97 | 100 | 100 | 86*¹ |
|  | 0.7 | 0 | 0 | 37 | 0 | 62 | 43 | 65 | 67 | 99 | 92 | 38*¹ |
|  | 0.28 | 0 | 0 | 27 | 0 | 25 | 0 | 35 | 30 | 63 | 80 | 5*¹ |

*F.B. = Field Bindweed
Jw. = Jimsonweed
P.S. = Prickly sida
Sp. = Sicklepod
Sw. = Smartweed
*¹Average of two test runs.

TABLE IV

TURF GRASS GROWTH INHIBITION
% Control

| No. | ppm | R | F | B | C |
|---|---|---|---|---|---|
| 5 | 400 | 0 | 56 | 56 | 21 |
|  | 160 | 0 | 27 | 54 | 0 |
|  | 64 | 0 | 0 | 21 | 0 |
| 6 | 400 | 15 | 52 | 65 | 30 |
|  | 160 | 0 | 0 | 0 | 0 |
|  | 64 | 0 | 0 | 0 | 16 |

R = Ryegrass
F = Creeping Red Fescue
B = Bluegrass
C = Crabgrass

Obviously, many modifications and variations of the invention, described hereinabove and below, can be made without departing from the essence and scope thereof.

What is claimed is:

1. A compound having the formula:

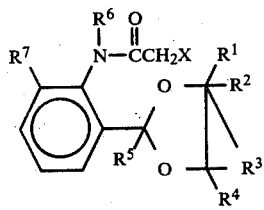

wherein
$R^1$ is alkyl having 1 to 4 carbon atoms;
$R^2$, $R^3$ and $R^4$ are individually hydrogen or alkyl having 1 to 4 carbon atoms;
$R^5$ is alkyl having 1 to 4 carbon atoms;
$R^6$ is hydrogen or alkyl having 1 to 4 carbon atoms;
$R^7$ is methyl; and X is chloro.

2. The compound according to claim 1 wherein $R^5$ is methyl, $R^1$ is ethyl and $R^2$, $R^3$ and $R^4$ are hydrogen.

3. The compound according to claim 1 wherein $R^5$ and $R^1$ are methyl and $R^2$, $R^3$ and $R^4$ are hydrogen.

4. The compound according to claim 1 wherein $R^5$, $R^1$, $R^2$ and $R^3$ are methyl and $R^4$ is hydrogen.

5. The compound of claim 1 wherein $R^5$ is methyl.

6. The compound of claim 5 wherein said compound is 2,4-dimethyl-2-(2-chloroacetamido-3-methylphenyl)-dioxolane.

7. The compound of claim 1 wherein said compound is 2,4-dimethyl-2(2-(N-methyl-chloroacetamido)-3-methylphenyl)dioxolane.

8. A herbicidal composition comprising a biologically inert carrier and a herbicidally-effective amount of a compound defined in claim 1.

9. A method of killing vegetation which comprises applying to said vegetation or its growth environment a herbicidally-effective amount of a compound defined in claim 1.

10. A method for retarding plant growth which comprises applying to plants or their growth environment a plant-growth retarding amount of a compound of the formula defined in claim 1.

11. A method for retarding the growth of Fescue, Bluegrass and Crabgrass which comprises applying to said plants or their growth environment a plant-growth retarding amount of a compound of the formula defined in claim 1.

12. A herbicidal composition comprising a biologically inert carrier and a herbicidally-effective amount of a compound defined in claim 7.

13. A method of killing vegetation which comprises applying to said vegetation or its growth environment a herbicidally-effective amount of a compound defined in claim 7.

14. A pre-emergence method for preventing or retarding the growth of grasses which comprises applying a herbicidally effective amount of the compound of claim 7 to the growth environment or potential growth environment of said grasses.

* * * * *